United States Patent [19]

Marsh et al.

[11] 4,251,325

[45] Feb. 17, 1981

[54] PROCESS FOR THE REMOVAL OF HYDROXYACETONE FROM PHENOL

[75] Inventors: Christopher R. Marsh, Grangemouth; James A. Russell, Edinburgh, both of Scotland

[73] Assignee: BP Chemicals Limited, London, England

[21] Appl. No.: 14,627

[22] Filed: Feb. 23, 1979

[30] Foreign Application Priority Data

Mar. 4, 1978 [GB] United Kingdom ............... 08662/78

[51] Int. Cl.³ .......................................... B01D 3/42
[52] U.S. Cl. ........................................ 203/2; 203/3; 568/754
[58] Field of Search ................... 568/754; 203/2, 3, 91

[56] References Cited

U.S. PATENT DOCUMENTS

| 3,672,961 | 6/1972 | Nixon | 568/754 |
| 3,896,006 | 7/1975 | Cooke | 568/754 |

*Primary Examiner*—Frank Sever

*Attorney, Agent, or Firm*—Brooks, Haidt, Haffner & Delahunty

[57] ABSTRACT

Phenol containing less than 30 ppm hydroxyacetone is produced by feeding hydroxyacetone-contaminated phenol obtained by the decomposition of cumene hydroperoxide, which phenol is substantially free from cleavage catalyst and light ends such as acetone and water, and up to 22% by weight of cumene and/or alpha-methyl styrene to an intermediate point in a distillation column from which there is removed overhead a fraction containing cumene and/or alpha-methyl styrene and a substantial proportion of the hydroxyacetone in the feed and there is removed from the base a fraction comprising phenol containing less than 30 ppm hydroxyacetone, whilst maintaining the column under such conditions of temperature and pressure that cumene and/or alpha-methyl styrene forms from 55 to 80% by weight of the composition on the uppermost 15 to 70% of the trays in the stripping section and phenol forms greater than 50% by weight of the composition on the bottommost 10 to 50% of the trays in the stripping section.

13 Claims, 1 Drawing Figure

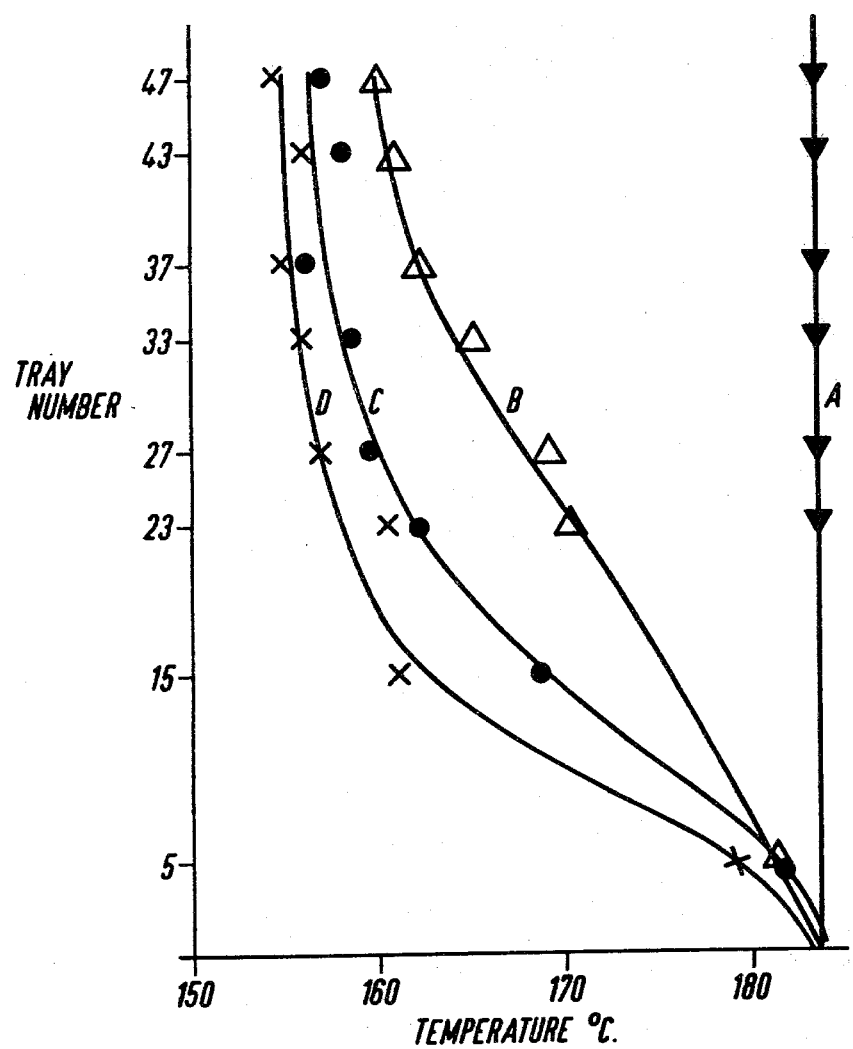

PROCESS FOR THE REMOVAL OF HYDROXYACETONE FROM PHENOL

The present invention relates to a process for the removal of hydroxyacetone from crude phenol obtained by the decomposition of cumene hydroperoxide.

An efficient industrialised process for producing phenol on a large scale is by the oxidation of isopropyl benzene, otherwise known as cumene, to cumene hydroperoxide, which is thereafter subjected to a cleavage reaction, generally in the presence of an acid catalyst, to produce as principal products, phenol and acetone. In addition to the principal products there are formed varying amounts of side-products such as mesityl oxide, alphamethyl styrene, alpha-methyl styrene dimers, para-cumyl phenol, phenyl dimethyl carbinol (carbinol), acetophenone, other high phenols and high-boilers. The cleavage product together with any unreacted cumene, collectively to be referred to hereinafter as the cumene hydroperoxide cleavage reaction product, after removal of any catalyst present, is subjected to a series of purification steps in which phenol and acetone are recovered.

Modern uses for phenol, such as its further conversion into diphenylolpropane, polycarbonates, caprolactam and chlorination products, require a highly pure material. It is inherent in the process hereinbefore described that a number of minor impurities are formed, either due to impurities in the feed cumene or as a result of side-reactions occurring at various stages of the process. Whilst most of these impurities can be removed by conventional steps, some are extremely difficult to separate from phenol. One such impurity is hydroxyacetone, also known as acetol, and its homologue acetoin. Although the concentration of this impurity in crude phenol is small, eg about 0.15%, many modern specifications require this to be reduced to less than 30 ppm and some specifications to less than 10 ppm. The presence of hydroxyacetone also affects another important specification value, namely the carbonyl value of the pure product. Finally, hydroxyacetone can condense with phenol under certain conditions, including normal storage conditions, to product 2-methylbenzofuran, which compound is particularly sensitive to chlorination. In the presence of 2-methylbenzofuran chlorination of phenol yields very dark coloured products which are undesirable. It is therefore desirable that the industrial scale purification of phenol should remove hydroxyacetone and related impurities as efficiently as possible.

Theoretically it would appear to be a simple matter to separate hydroxyacetone (b.p. 145° C./760 mm) from phenol (b.p. 182° C./760 mm) by distillation. In practice, complete separation has been found to be almost impossible because of polar interaction between the compounds. Many attempts have been made to provide a satisfactory separation and although some such methods are believed to be used in commercial practice, all are deficient in some respect. Thus British Pat. No. 920,905 describes the purification of phenol by treatment with alkali and $FeCl_3$, U.S. Pat. No. 2,910,511 describes the treatment of crude phenol with silica alumina, U.S. Pat. No. 3,965,187 discloses the treatment of phenol with polyamines and U.S. Pat. No. 2,971,893 teaches the treatment of phenol with alkali and hydrogen peroxide. A very successful method based on thermal treatment, preferably in the presence of iron salts, to convert hydroxyacetone to higher boiling products which are more readily removed is described in British Pat. Nos. 865,677 and 933,723. Other chemical methods, such as oxidation in the presence of ammonia and treatment to form oximes or hydrazones have been suggested. All these methods suffer from the disadvantage of introducing foreign chemicals and thereby still further impurities into the process and moreover, they are expensive to operate. More recently attempts have been made to effect the separation by distillation alone. Thus British Patent No. 1,021,759 describes and claims a process for the manufacture of highly pure phenol wherein a product obtained by the oxidation of cumene and the decomposition of its hydroperoxide is fed to a distillation column and phenol free from impurity is taken from the bottom of the column, characterised in that the distillation is carried out in such manner that said feed contains at least 0.28 parts by weight of cumene per part by weight of phenol and part of the column above the feeding point is maintained at least at a temperature of more than 110° C. under atmospheric pressure. In the Examples the amount of hydroxyacetone in the bottoms products varies from 30 to 60 ppm. These hydroxyacetone levels are unacceptably high for modern usage. Furthermore the process requires the recycle of substantial amounts of cumene which is expensive in terms of both capital and utilities.

It has now been found that phenol containing less than 30 ppm hydroxyacetone can be obtained by distillation, without recycle of excessive amounts of cumene and without the need for strict control of the composition of the feed to the column, by controlling the composition on particular trays of the distillation column.

Thus the present invention provides a process for the removal of hydroxyacetone from hydroxyacetone-contaminated phenol obtained by the decomposition of cumene hydroperoxide, which phenol is substantially free from cleavage catalyst and light ends comprising acetone and water, which process comprises feeding the phenol and cumene and/or alpha-methyl styrene in a concentration up to 22% by weight to an intermediate point in a distillation column provided with conventional reboiler, condensing and refluxing facilities, removing overhead a fraction comprising cumene and/or alpha-methyl styrene and a substantial proportion of the hydroxyacetone in the feed and removing as a base product a fraction comprising phenol containing less than 30 ppm hydroxyacetone whilst maintaining the column under such conditions of temperature and pressure that cumene and/or alpha-methyl styrene forms from 55 to 80% by weight of the composition on the uppermost 15 to 70% of the trays in the stripping section and phenol forms greater than 50% by weight of the composition on the bottommost 10 to 50% of the trays in the stripping section.

That portion of the distillation column above the feed-point is universally recognised in the art as the rectification section of the column and that portion below the feed-point as the stripping section. The number of trays in the rectification section of the column is not directly relevant to the process of the present invention provided there are sufficient trays to perform the rectification operation. For the avoidance of doubt, the trays in the stripping section are counted upwards from the base of the column and as a result the uppermost trays are those immediately below the feedpoint and the bottommost trays are those at the base of the column.

The feed to the column for the removal of hydroxyacetone is hydroxyacetone-contaminated phenol obtained by the decomposition of cumene hydroperoxide, which phenol is substantially free from catalyst and light ends comprising acetone and water, and up to 22% by weight of cumene and/or alpha-methyl styrene. Preferably the feed contains from 1 to 20, even more preferably from 5 to 15% by weight of cumene and/or alpha-methyl styrene. A suitable feed is the residue fraction containing phenol, cumene, alpha-methyl styrene, carbinol, acetophenone, higher phenols, alphamethyl styrene dimers and high-boilers recovered from the base of a column separating overhead a fraction containing material in the cumene hydroperoxide cleavage reaction product, as hereinbefore defined, after removal of cleavage catalyst therefrom, having a boiling point lower than that of phenol, including acetone, water, most of the mesityl oxide, cumene and alpha-methyl styrene in addition to the practical minimum content of phenol, normally below 1% by weight. The residue fraction recovered from the base of the column generally contains from 1 to 8% by weight of hydrocarbon and up to 0.2% by weight of hydroxyacetone. Alternatively the fraction recovered from the base of the column may be further purified before feeding to the column removing hydroxyacetone by: A. feeding to a distillation column wherein there is removed an overhead fraction containing phenol, cumene and/or alpha-methyl styrene, hydroxyacetone and less than 1000 ppm (weight) in total of acetophenone and carbinol and a fraction containing phenol, acetophenone, carbinol and high-boilers is removed as a bottoms fraction, B. feeding the bottoms fraction from A to a cracking zone maintained at a temperature of, for example, 300° to 400° C. wherein higher-boiling compounds are partially decomposed to phenol and cumene and/or alpha-methyl styrene, C. passing the product containing acetophenone in addition to decomposition products and uncracked material from B to a further distillation column in which an overhead fraction comprising phenol and cumene and/or alpha-methyl styrene is separated from acetophenone and other high-boiling compounds and thereafter recycling the overhead fraction to the washing section preceding feeding to the distillation.

The overhead fraction comprising phenol and hydrocarbon from A generally contains from 1 to 8% by weight hydrocarbon and up to 0.2% by weight hydroxyacetone. It is this fraction which may be used as feed to the hydroxyacetone removal column in the process of the present invention.

The preferred feed to the column removing hydroxyacetone is the crude phenol side stream fraction obtained by feeding the catalyst-free product obtained by the decomposition of cumene hydroperoxide to an intermediate point in a distillation column provided with conventional reboiler, condensing and refluxing facilities separating, in the upper section thereof, phenol from a crude acetone fraction and, in the lower section thereof, phenol from a fraction containing materials of higher boiling point than phenol, including acetophenone and carbinol and removing: D. overhead a crude acetone fraction, E. from the base a fraction containing acetophenone, carbinol, phenol and higher boiling compounds and F. from a point in the column above the feed-point wherein the total concentration of acetophenone plus carbinol in the phenol is reduced to less than 1000 ppm (weight), a sidestream fraction comprising crude phenol.

Further details of this process for producing crude phenol may be found in our copending application No. 48075/76 (BP Case No. 4271). Generally the crude phenol sidestream fraction, which is the preferred feed in the process of the present invention, contains from 1 to 8% by weight of cumene and/or alpha-methyl styrene and up to 2000 ppm hydroxyacetone.

It is also possible to purify a catalyst-free phenol fraction, contaminated with hydroxyacetone but otherwise free from light ends comprising acetone and water and additionally free from cumene and/or alpha-methyl styrene, by the addition of the requisite quantity of cumene and/or alpha-methyl styrene to the phenol fraction before or during distillation.

Preferably the hydroxyacetone removal column is maintained under such conditions of temperature and pressure that cumene and/or alpha-methyl styrene forms from 55 to 80% by weight of the composition on the uppermost 20 to 50% of the trays in the stripping section and phenol forms greater than 50% by weight in the composition on the bottommost 20 to 50% of the trays in the stripping section.

Thus a preferred embodiment of the present invention provides a process for the removal of hydroxyacetone from hydroxyacetone contaminated phenol obtained by the decomposition of cumene hydroperoxide, which phenol is substantially free from cleavage catalyst and light ends comprising acetone and water, which process comprises feeding the phenol together with cumene and/or alpha-methyl styrene in a concentration in the range from 5 to 15% by weight to an intermediate point in a distillation column provided with conventional reboiler, condensing and refluxing facilities and containing about 50 trays below the feedpoint, removing overhead a fraction comprising cumene and/or alpha-methyl styrene and a substantial proportion of the hydroxyacetone in the feed and removing as a base product a fraction comprising phenol containing less than 30 ppm hydroxyacetone, whilst maintaining the column under such conditions of temperature and pressure that cumene and/or alpha-methyl styrene forms from 65 to 75% by weight of the composition on the uppermost 20 trays in the stripping section and phenol forms greater than 50% by weight of the composition on the bottommost 20 trays in the stripping section.

If the column is operated in such a way that all the cumene and/or alpha-methyl styrene in the feed is taken overhead, which is easy to achieve by maintaining all the stripping trays at about 180° C. is near the boiling point of phenol, not only will a large proportion of the phenol fed to the column be taken overhead, but also, despite the high temperature, as much as 300 ppm of hydroxyacetone will be left in the base product. On the other hand if the temperature of the stripping trays is kept too low most of the cumene and/or alpha-methyl styrene appears in the base product together with an excessive proportion of the hydroxyacetone. The process of the present invention strikes a balance between these two extremes. Thus the fraction removed overhead will contain the bulk of the cumene and/or alpha-methyl styrene and hydroxyacetone in the feed to the column, but only up to 1%, usually less than 0.5% by weight of the phenol in the feed, and the fraction removed as a base product will contain not only the bulk of the phenol containing less than 30 ppm hydroxyacetone, but also up to 10% by weight of the cumene and/or alpha-methyl styrene in the feed. However, and this is the major advantage to be gained by operating in a manner according to the invention, the base product may contain less than 10 ppm hydroxy acetone.

By operating according to the present invention those trays immediately below the feed-point are rich in cumene and/or alphamethyl styrene and the trays immediately above the base are rich in phenol. In between there will be a gradation, working up the column, from a phenol-rich to a hydrocarbon-rich composition on the trays, and in one section of the column, hereafter to be referred to as the breakpoint section, there will be a rapid change in the composition of the liquid on the trays.

The operating conditions of temperature and pressure which result in the aforesaid compositions on specific trays in the stripping section are capable of some variation but require careful control. Thus, while atmospheric pressure is preferred, the column may be operated at sub- or super-atmospheric pressure with corresponding adjustments to the temperature ranges. Since the temperature of specific trays in the stripping section varies according to the pressure drop across the column, which in turn depends upon the number of trays in the column, it is difficult to generalise this parameter. The temperature of any specific tray in the break-point section of the stripping section should be controlled with ±5, preferably ±2° C. of a constant temperature, which may be, for example, in the range 155° to 165° C. for a column containing 65 trays of which 50 are below the feed-point, ie in the stripping section, when the column is operated under atmospheric pressure conditions.

The temperature of a particular tray in the break-point section of the column may, for example, be maintained within the desired limits by providing the tray with a temperature controller which functions to adjust either the reflux ratio or the heat applied to the base of the column, thereby maintaining the necessary tray compositions.

The following Examples and Comparison Tests will now serve to illustrate the process of the present invention.

COMPARISON TEST 1

To a column equipped with conventional reboiler, condensing and refluxing facilities and containing 65 trays was fed on tray number 50 (counting upwards from the base of the column) 850 parts/hour of a feed having the composition in Table 1. The temperature profile in the stripping section of the column is shown as curve B in the Figure and the tray compositions under these conditions are shown in Table 1. The overhead take-off rate was 98.6 parts/hour and the reflux ratio (R/D) was 18. Tray pressure were slightly in excess of atmospheric.

As can be seen from Table 1 and the Figure the column was operated with a relatively high temperature profile in the stripping section. Under these conditions hydrocarbon did not represent from 55 to 80% by weight of the composition on each of the 7 (≡15%) trays immediately below the feed-point. The phenol removed from the base of the column contained 176 ppm of hydroxyacetone.

This is not an example according to the invention and is included only for the purpose of comparison.

COMPARISON TEST 2

Comparison Test 1 was repeated except that a very high temperature profile in the stripping section, as shown in curve A of the Figure, was used.

Under these conditions the base product was found to contain 300 ppm of hydroxyacetone.

This is not an example according to the invention and is included only for the purpose of comparison.

EXAMPLE 1

To a column equipped with conventional reboiler, condensing and refluxing facilities and containing 65 trays was fed on tray number 50 (counting upwards from the base of the column) 386 parts/hour of a feed having the composition shown in Table 2. The overheat take-off rate was 33 parts/hour and the reflux ratio (R/D) was 29. The temperatures at various trays in the stripping section and the tray compositions at these temperatures are shown in Table 2.

The hydrocarbon concentration in the stripping section was allowed to build up to a relatively high value with over 70% by weight hydrocarbon in the composition on the trays as low down as tray 23, the control tray. The phenol withdrawn as base product still contained only 12 ppm of hydroxyacetone and only 0.14 wt % of the phenol fed to the column appeared in the hydrocarbon distillate.

EXAMPLE 2

To a column equipped with conventional reboiler, condensing and refluxing facilities and containing 65 trays in total was fed on tray number 50 (counting upwards from the base of the column) about 510 parts/hour of phenol containing 1020 ppm hydroxyacetone and 11.8 wt % of total hydrocarbon. The overhead take-off rate was 45.7 parts/hour and the reflux ratio (R/D) was 17:1. The temperature profile in the stripping section of the column is shown as curve C in the Figure. On each of at least the upper 8 trays of the stripping section hydrocarbon constituted from 50 to 80% by weight of the composition, judging by the temperature profile.

The phenol withdrawn from the base of the column contained 22 ppm of hydroxyacetone. The overhead fraction contained only 0.27 wt % of the phenol fed to the column in addition to hydrocarbon and hydroxyacetone.

EXAMPLE 3

To a column equipped with conventional reboiler, condensing and refluxing facilities and containing 65 trays in total was fed on tray number 50 (counting upwards from the bottom of the column) 346 parts/hour of phenol containing 1800 ppm hydroxyacetone and 6 wt % hydrocarbon. The overhead take-off rate was about 40 parts/hour and the reflux ratio (R/D) was 22:1. The temperature profile in the stripping section of the column is shown as curve D in the Figure. This corresponds to a very high hydrocarbon loading of the stripping trays, even down to tray 10.

The phenol removed from the base of the column contained only 6 ppm of hydroxyacetone. A hydrocarbon fraction was removed overhead.

TABLE 1

| Tray No. | Temperature (°C.) | Component concentrations (wt %) | | | | | |
|---|---|---|---|---|---|---|---|
| | | Hydroxyacetone | Phenol | Total measured hydrocarbon | Cumene | Alpha-methyl styrene | t-butyl benzene |
| Feed | — | 0.103 | approx 90 | | 5.6 | 0.5 | |
| 23 | 170 | 0.10 | | 43.2 | 1.15 | 38.6 | 3.41 |
| 27 | 169 | — | | — | — | — | — |
| 33 | 165 | 0.19 | | 44.3 | 15.35 | 26.07 | 2.86 |
| 37 | 162 | 0.18 | | 49.2 | 30.0 | 17.21 | 2.02 |
| 43 | 161 | 0.15 | | 52.7 | 46.7 | 5.4 | 0.57 |
| 47 | 160 | — | | — | — | — | — |

—in the Table indicates that no sample was taken.

TABLE 2

| Tray No | Temperature (°C.) | Component concentrations (wt %) | | | | | |
|---|---|---|---|---|---|---|---|
| | | Hydroxyacetone | Phenol | Total measured hydrocarbon | Cumene | Alpha-methyl styrene | t-butyl benzene |
| Feed | | 0.180 | approx 87 | | 5.5 | 0.5 | |
| 23 | 159.5 | 0.0002 | | 71.2 | 65.5 | 4.87 | 0.81 |
| 27 | 156.5 | 0.0001 | | 71.5 | 69.4 | 1.87 | 0.25 |
| 33 | 156 | 0.0002 | | 75.8 | 75.5 | 0.30 | 0.04 |
| 37 | 154.5 | 0.0013 | | 75.7 | 75.6 | 0.09 | 0.01 |
| 43 | 155.5 | 0.011 | | 77.0 | 76.9 | 0.05 | N.A. |
| 47 | 155 | 0.081 | | 78.8 | 78.7 | 0.05 | N.A. |

N.A. in the Table indicates that no analysis was made.

We claim:

1. A process for the removal of hydroxyacetone-contaminated phenol obtained by the decomposition of cumene hydroperoxide, which phenol is substantially free from cleavage catalyst and light ends comprising acetone and water, which process comprises feeding said phenol and cumene and/or alpha-methyl styrene in a concentration up to 22% by weight to an intermediate point in a single distillation column provided with conventional reboiler, condensing and refluxing facilities, removing overhead a fraction comprising cumene and/or alphamethyl styrene and a substantial proportion of the hydroxyacetone in the feed and removing as a base product a fraction comprising phenol containing less than 30 ppm hydroxyacetone whilst controlling the temperature and pressure conditions in said single column so that cumene and/or alpha-methyl styrene forms from 55 to 80% by weight of the composition on the uppermost 15 to 70% of the trays in the stripping section and phenol forms greater than 50% by weight of the composition on the bottommost 10 to 50% of the trays in the stripping section.

2. A process according to claim 1 wherein said feed contains from 1 to 20% by weight of cumene and/or alpha-methyl styrene.

3. A process according to claim 1 wherein said feed contains from 5 to 15% by weight of cumene and/or alpha-methyl styrene.

4. A process according to claim 1 wherein said feed is the residue fraction containing phenol, cumene, alpha-methyl styrene, carbinol, acetophenone, higher phenols, alpha-methyl styrene dimers and highboilers recovered from the base of a column separating overhead a fraction containing material in the cumene hydroperoxide cleavage product, after removal of cleavage catalyst therefrom, having a boiling point lower than that of phenol, including acetone, water, most of the mesityl oxide, cumene and alpha-methyl styrene in addition to the practical minimum content of phenol.

5. A process according to claim 4 wherein said residue fraction contains from 1 to 8% by weight of cumene plus alpha-methyl styrene and up to 0.2% by weight of hydroxyacetone.

6. A process according to claim 4 wherein said residue fraction recovered from the base of said column is further purified by feeding to a distillation column wherein there is removed an overhead fraction containing phenol, cumene and/or alpha-methyl styrene, hydroxyacetone and less than 1000 ppm (weight) in total of acetophenone and carbinol and a fraction containing phenol, acetophenone, carbinol and highboilers is removed as a bottoms fraction, said overhead fraction being used as feed to said distillation column from which phenol substantially free from hydroxyacetone is removed as a base product.

7. A process according to claim 1 wherein said feed is the crude phenol sidestream fraction obtained by feeding the catalyst-free product obtained by the decomposition of cumene hydroperoxide to an intermediate point in a distillation column provided with conventional reboiler, condensing and refluxing facilities separating, in the upper section thereof, phenol from a crude acetone fraction and, in the lower section thereof, phenol from a fraction containing materials of higher boiling-point than phenol, including acetophenone and carbinol and removing, overhead, a crude acetone fraction, from the base, a fraction containing acetophenone, carbinol, phenol and higher boiling compounds and, from a point in said column above the feed-point wherein the total concentration of acetophenone plus carbinol in the phenol is reduced to less than 1000 ppm (weight), a sidestream fraction comprising crude phenol.

8. A process according to claim 7 wherein said crude phenol contains from 1 to 8% by weight of cumene and/or alpha-methyl styrene and up to 2000 ppm hydroxyacetone.

9. A process according to claim 1 wherein said column from which phenol substantially free from hydroxyacetone is removed as a base fraction is maintained under such conditions of temperature and pressure that cumene and/or alpha-methyl styrene forms from 55 to 80% by weight of the composition on the uppermost 20 to 50% of the trays in the stripping section and phenol forms greater than 50% by weight in the composition on the bottommost 20 to 50% of the trays in the stripping section.

10. A process for the removal of hydroxyacetone from a hydroxyacetone-contaminated phenol obtained by the decomposition of cumene hydroperoxide, which phenol is substantially free from cleavage catalyst and light ends comprising acetone and water, which process comprises feeding said phenol together with cumene and/or alpha-methyl styrene in a concentration in the range from 50 to 15% by weight to an intermediate point in a single distillation column provided with conventional reboiler, condensing the refluxing facilities and containing about 50 trays below the feed-point, removing overhead a fraction comprising cumene and/or alpha-methyl styrene and a substantial proportion of the hydroxyacetone in the feed and removing as a base product a fraction comprising phenol containing less than 30 ppm hydroxyacetone, whilst controlling the conditions of temperature and pressure in said column so that cumene and/or alpha-methyl styrene forms from 65 to 75% by weight of the composition on the uppermost 20 trays in the stripping section and phenol forms greater than 50% by weight of the composition on the bottommost 20 trays in the stripping section.

11. A process according to claim 10 wherein said column is maintained at atmospheric pressure.

12. A process according to claim 10 wherein the temperature of any specific tray in the break-point section of the stripping section is controlled within ±5° C. of a constant temperature in the range 155° to 165° C.

13. A process according to claim 12 wherein said temperature is controlled by providing said tray with a temperature controller which functions to adjust either the reflux ratio or the heat applied to the base of said column.

* * * * *